United States Patent [19]
Plonka et al.

[11] 3,974,199
[45] Aug. 10, 1976

[54] PROCESS FOR PRODUCTION OF CYCLOPROPYLCYANIDE

[75] Inventors: James H. Plonka; R. Garth Pews, both of Midland, Mich.

[73] Assignee: The Dow Chemical Company, Midland, Mich.

[22] Filed: June 16, 1975

[21] Appl. No.: 587,013

[52] U.S. Cl. .............................................. 260/464
[51] Int. Cl.² .............. C07C 120/04; C07C 121/46
[58] Field of Search .................................... 260/464

[56] References Cited
UNITED STATES PATENTS

| | | | |
|---|---|---|---|
| 3,546,295 | 12/1970 | Maravetz | 260/464 X |
| 3,725,458 | 4/1973 | Starks | 260/465.1 |
| 3,739,025 | 6/1973 | Linder et al. | 260/464 X |
| 3,843,709 | 10/1974 | Bacha et al. | 260/464 |
| 3,853,942 | 12/1974 | Sury et al. | 260/464 |

OTHER PUBLICATIONS

Schlatter, J. Org. Syn., Coll. 3, pp. 223–225, 1955.
Cloke, et al., J.A.C.S., 53, 1931, pp. 2791–2796.

*Primary Examiner*—Joseph P. Brust
*Attorney, Agent, or Firm*—Gary R. Plotecher

[57] ABSTRACT

Cyclopropylcyanide is prepared by an improved process comprising reacting by contacting a γ-halobutyronitrile or mixture thereof, with an alkali metal hydroxide in the presence of a catalytic amount of an onium salt. For example, the reaction of 4-chlorobutyronitrile with sodium hydroxide in the presence of benzyltriethylammonium chloride produces cyclopropylcyanide in high yield.

9 Claims, No Drawings

PROCESS FOR PRODUCTION OF CYCLOPROPYLCYANIDE

This invention relates to the art of preparing cyclopropylcyanide. More specifically, this invention is directed to the process for preparing cyclopropylcyanide by means of an onium salt catalyst.

The production of cyclopropylcyanide, although old in the art, has a history of low to moderate yields and/or complicated techniques. It was first prepared by M. L. Henry by distillation of γ-chlorobutyronitrile over dry potassium hydroxide. Rec. Trav. Chem., 18, p 228 (1898). However, product loss through hydrolysis and polymerization suppressed yields. Later, yields were improved (although not satisfactorily) by use of exacting recovery techniques and the substitution of sodamide for potassium hydroxide J. Am. Chem. Soc., 53, p 2791 (1931); Org. Syn. Coll., 3, p 223 (1955). Recently, good yields have been obtained by the use of an aprotic solvent, Bacha et al. (U.S. Pat. No. 3,843,709) and/or substituting alkoxide for alkali metal hydroxide, Sury and Grace (U.S. Pat. No. 3,853,942). However, these cited methods for improved or good yields still require the use of solvents and their eventual separation from the product.

According to the present invention both high yield and simplified techniques are achieved by a process for preparing cyclopropylcyanide which comprises reacting by contacting a γ-halobutyronitrile with an alkali metal hydroxide in the presence of an onium salt catalyst. Said catalyst facilitates the dehydrohalogenation of γ-halobutyronitrile and its resultant cyclization to cyclopropylcyanide. Although water is needed, that typically found in reagent grade sodium hydroxide is sufficient. Organic solvents of any kind are unnecessary and, as such, complicated separation techniques for their removal are avoided. However, benzene and the like will not impede the process. Temperature, pressure, and stoichiometry are not critical to the process and may be varied as desired by the individual practitioner. Moreover, the reaction time required for quantitative conversion of γ-halobutyronitrile to cyclopropylcyanide is minimized.

Accordingly, it is an object of this invention to provide a process for the production of cyclopropylcyanide wherein the yield of same is maximized.

Another object of this invention is to provide a process for the production of cyclopropylcyanide wherein the need for an organic solvent is eliminated.

Still a further object of this invention is to provide a process for the production of cyclopropylcyanide wherein the need for complicated separations is eliminated.

These and other objects of the invention will become apparent to one skilled in the art after studying the following detailed description and appended claims.

The γ-halobutyronitriles which are used as a source material in the practice of this invention include 4-chlorobutyronitrile, 4-bromobutyronitrile, 4-iodobutyronitrile and combinations thereof. Because the 4-iodo- material is susceptible to displacement reactions, 4-chloro- and 4-bromobutyronitrile are preferred, with the former especially preferred.

Any known and suitable alkali metal hydroxide can be used in the instant process but the sodium and potassium hydroxides are the most familiar and therefore preferred. Mixtures of such alkali metal hydroxides are acceptable.

The catalysts here used are organic onium salts selected from the group consisting of a quaternary ammonium salt and a quaternary phosphonium salt. These salts are known in the art as phase-transfer catalysts and are described in such publications as the J. Am. Chem. Soc. 93, 195 (1971) and in British patent (1,227,144) by Starks and Napier. The ammonium salts are preferred over the phosphonium salts and benzyltriethyl-, benzyltri-n-butyl-, and tetra-n-butylammonium chlorides and bromides are most preferred.

To further illustrate the type of onium salts used, suitable onium salts are represented by the formula

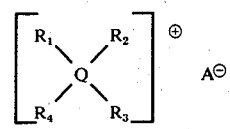

wherein: Q is a quaternized nitrogen or phosphorus atom, A is a neutralizing anion, and $R_1$-$R_4$ are hydrocarbyl groups of from 1 to about 16 carbon atoms each with a combined minimum total of about 10 carbon atoms. The hydrocarbyl groups include, but are not limited to, alkyl, aryl, alkylaryl, arylalkyl, cycloalkyl, and the like. Furthermore, $R_1$ can join with $R_2$, or $R_2$ with $R_3$, etc. to form a 5- or 6-membered heterocyclic compound having at least one quaternized nitrogen or phosphorus atom in the ring and said ring may also contain one nonadjacent atom of nitrogen, oxygen or sulfur.

The neutralizing anion portion of the salt, i.e., $A^\ominus$ in the above generic formula, may be varied to convenience. Chloride and bromide are the preferred anions, but other representative anions include fluoride, iodide, tosylate, acetate, bisulfate, etc. The following compounds are illustrative: tetraalkylammonium salts, such as tetra-n-butyl-, tetrahexyl-, and trioctylmethyl-, hexadecyltriethyl-, and tridecylmethylammonium chlorides, bromides, iodides, bisulfates, tosylates, etc; arylalkylammonium salts, such as tetrabenzylammonium chloride, benzyltrimethyl-, benzyltriethyl-, benzyltributyl-, and phenethyltrimethylammonium chlorides, bromides, iodides, etc; arylammonium salts, such as triphenylmethylammonium fluoride, chloride or bromide, N,N,N-trimethylanilinium chloride, N,N,N-triethylanilinium bromide, N,N-diethyl-N-ethylanilinium bisulfate, trimethylnaphthylammonium chloride, p-methylphenyltrimethylammonium chloride or tosylate, etc.; 5- and 6-membered heterocyclic compounds containing at least one quaternary nitrogen atom in the ring, such as N,N,N', N' - tetramethylpiperaziniumdichloride, N-methylpiperaziniumdichloride, N-hexylpiperazinium iodide, 4-pyridyltrimethylammonium iodide, N,N-dibutylmorpholinium chloride, N-ethylthiazolium chloride, N-butylpyrrolium chloride, etc., and the corresponding phosphonium salts.

The γ-halobutyronitrile and the alkali metal hydroxide can be used in any suitable ratio to achieve the desired product. Although equimolar amounts can be used, it is generally preferred to have an excess of the alkali metal hydroxide because said excess maintains a reasonably uniform reaction rate through consumation of the source material. Thus, the mole ratio of alkali metal hydroxide to γ-halobutyronitrile should be at least about 1 to 1 and preferably at least about 1.1 to 1. As an upper limit, a mole ratio of about 1.5 to 1 and preferably about 1.3 to 1 can be employed.

The amount of the onium salt required is a catalytic amount. This amount is at least about 0.25 percent by weight based on the weight of the reactants with a preferred lower limit of about 1 percent. There is no theoretical upper limit but practical problems of solubility and separation indicate that the catalyst should not exceed about 10 weight percent, with a preferred upper limit of about 5 weight percent.

The temperature and pressure at which the process is conducted are not critical and thus can be selected as desired. For example, the process can be conducted at autogenous pressure and at a temperature at which the reaction mass is a liquid. However, it is generally preferred that the process be conducted at a temperature of at least about 70°C, with a upper limit of about 85°C, since best yields are thus obtained.

At least trace amounts of water are necessary to the invention. The water present in reagent grade alkali metal hydroxide (about 5 percent) is sufficient and preferred. However, water may be present up to about 10 percent of the reaction mass without adversely affecting the process.

The invention is conducted in the absence of any organic solvent. However, if a solvent is desired, any one stable to the reaction conditions can be employed without detriment to the process. Illustrative solvents are benzene, aryl halides, such as 0-dichlorobenzene, 1,2,4-trichlorobenzene, bromobenzene, etc., paraffins and cycloparaffins, such as heptane, octane, decane, cyclohexane, etc., alkyl halides, such as dichloromethylene, chloroform, and carbontetrachloride, etc., and the like.

The following examples are illustrative of certain specific embodiments of the invention. However, these examples are for illustrative purposes only and should not be construed as limitations upon the invention.

EXAMPLE 1

A 50 ml, 3-neck round-bottom flask was fitted with a magnetic stirrer, a thermometer, and a reflux condenser. The flask was then charged with 10.4 g of 4-chlorobutyronitrile, 4 g of ground sodium hydroxide pellets and 0.5 g of benzyltriethylammonium chloride (BTEAC). The solution was refluxed at 78°C with stirring for 6 hours, then cooled. The crude solution was suction filtered and the organic phase was examined by gas chromatography and NMR. The results showed 99 percent cyclopropylcyanide and 1 percent unreacted 4-chlorobutyronitrile.

The filtered solids were then dissolved in water and titrated with 0.1N hydrochloric acid to a phenolphthalein end point for residual hydroxide ion. The results showed 0.1 g remaining.

EXAMPLE 2

A 100 ml, 3-neck round-bottom flask was fitted with a magnetic stirrer, a thermometer, and a reflux condenser. The flask was then charged with 10.4 g of 4-chlorobutyronitrile, 4 g of ground sodium hydroxide pellets, 25 ml of benzene and 0.5 g of benzyltriethylammonium chloride (BTEAC). The solution was refluxed with stirring for 6 hours, then cooled. The crude solution was suction filtered and examined by gas chromatography and NMR. The results showed 94 percent cyclopropylcyanide and 6 percent unreacted 4-chlorobutyronitrile.

The filtered solids were then analyzed as is Example 1 and showed 0.04 g of hydroxide ion remaining.

CONTROL A

The process of Example 1 was repeated except BTEAC was omitted. The results showed 28 percent cyclopropylcyanide. This illustrates that the onium salt is clearly a catalyst for the reaction.

EXAMPLE 3

The process of Example 1 is repeated except that benzyltriphenylphosphonium chloride is substituted for BTEAC to obtain a similarly high conversion of 4-chlorobutyronitrile to cyclopropylcyanide.

Although the invention has been described in considerable detail, it must be understood that such detail is for the purpose of illustration only and that many variations and modifications can be made by one skilled in the art without departing from the spirit and scope of the invention.

What is claimed is:

1. A process for the preparation of cyclopropylcyanide comprising reacting by contacting a γ-halobutyronitrile selected from the group consisting of 4-chlorobutyronitrile, 4-bromobutyronitrile, 4-iodobutyronitrile, and combinations thereof, with an alkali metal hydroxide in the presence of at least a trace amount of water and a catalytic amount of an onium salt of the formula

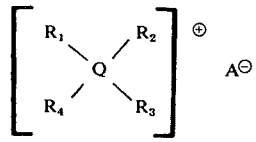

wherein: Q is a quaternized nitrogen or phosphorus atom, $A^\ominus$ is a neutralizing anion, and $R_1$-$R_4$ are hydrocarbyl groups of from 1 to about 16 carbon atoms each with a combined minimum total of about 10 carbon atoms, at an alkali metal hydroxide to γ-halobutyronitrile mole ratio of between about 1 to 1 and 1.5 to 1 and at a temperature at which the γ-halobutyronitrile, alkali metal hydroxide and onium salt are liquid.

2. The process of claim 1 wherein the γ-halobutyronitrile is 4-chlorobutyronitrile.

3. The process of claim 1 wherein the alkali metal hydroxide is sodium or potassium hydroxide.

4. The process of claim 1 wherein the onium salt catalyst is benzyltriethylammonium chloride.

5. The process of claim 1 wherein the mole ratio of alkali metal hydroxide to 65 -halobutyronitrile is between about 1.1 to 1 and about 1.3 to 1.

6. The process of claim 1 wherein the onium salt catalyst is present in an amount from about .25 to about 10 weight percent based on the total weight of the reactants.

7. The process of claim 1 wherein the onium salt catalyst is present in an amount from about 1 to about 5 weight percent based on the total weight of the reactants.

8. The process of claim 1 wherein the contacting is conducted at a temperature of between about 70°C and about 85°C, at autogenous pressure, and in the absence of an organic solvent.

9. The process of claim 7 wherein water is present in an amount between about that found in reagent grade alkali metal hydroxide and about 10 percent of the reaction mass.

* * * * *